Aug. 18, 1964 W. E. DUFFETT Plant Pat. 2,437
CHRYSANTHEMUM PLANT
Filed Oct. 4, 1963
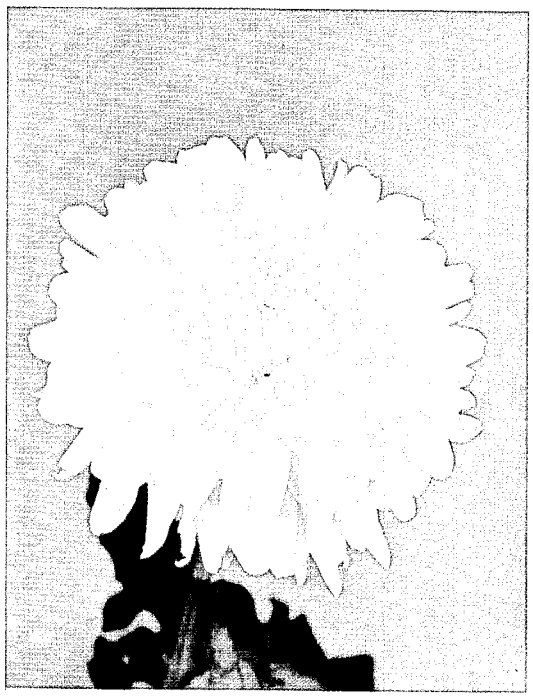
INVENTOR.
W. E. DUFFETT
By Robb & Robb
attorneys United States Patent Office Plant Pat. 2,437
Patented Aug. 18, 1964

2,437
CHRYSANTHEMUM PLANT

William E. Duffett, Barberton, Ohio, assignor, by mesne assignments, to George J. Ball, Inc., West Chicago, Ill.

Filed Oct. 4, 1963, Ser. No. 314,082
1 Claim. (Cl. Plt.—78)

My present invention comprises a new and distinct variety of chrysanthemum plant which is a sport of the variety disclosed in Plant Patent No. 2,007.

The instant chrysanthemum plant was discovered during the course of reproduction in growth of chrysanthemums on a production basis under somewhat different conditions from those which resulted in the parent plant, the parent plant having been specifically developed during the course of a very intensive program of hybridization and cross breeding, which program has been devoted to the improvement of both form, color and plant growth.

Whereas the instant variety was discovered under the conditions of growth at Barberton, Ohio, the parent variety originated in the vicinity of Niles, Michigan, and the primary difference between the instant variety and its parent, is the color of the bloom which is presented when viewed from a distance, and the characteristics of the parent are in most respects maintained and reproduced in this instant variety.

The color of my new variety is a brilliant to vivid yellow, appropriate reference to the color fan known as the Nickerson Color Fan published by The Munsell Color Company having been resorted to in order to describe said color. As the variety has been grown in the vicinity of Barberton, Ohio, under uniform culture, plants of my new variety produce large flowers on long, strong stems, very early and continuously for a long time, usually until the first hard frost.

By way of comparison with another chrysanthemum grown in the same general conditions, the instant variety may be compared with the variety of Plant Patent No. 2,274, in which it has been found that the instant variety makes a much better fall flowering chrysanthemum for cut flower purposes, because it produces a larger flower that is more resistant to outside weather conditions than that of the Plant Patent No. 2,274 variety.

The instant variety is an improvement over the variety of Plant Patent No. 2,274 inasmuch as it does produce the larger flower mentioned and because of its resistance to weather conditions.

Under the conditions of culture previously referred to, as existing in the vicinity of Barberton, Ohio, under which this new variety was discovered and has been grown, my new variety blooms early and profusely as well as continuously in the fall of the year.

My new variety may be said to be characterized by the brilliant to vivid yellow color of its blooms, double petalage, strong habit of growth and blooms on long, strong stems, reference being had to the Nickerson Color Fan as before noted for color comparison.

The blooms of my new variety are large and when fully expanded reach a size of 5½ inches in diameter and the plant in shrub form grows to a height of approximately 30 inches on the average.

My new variety has been asexually reproduced by stem cuttings in the vicinity of Barberton, Ohio, and my new variety has been found to retain its distinctive characteristics through successive asexual reproductions.

The accompanying drawing forming a part hereof shows a typical bloom of my new variety of chrysanthemum.

The following is a detailed description of my new variety of chrysanthemum plant, the color references being to the Nickerson Color Fan published by The Munsell Color Company:

Parentage: Sport of Plant Patent No. 2,007 variety.
Classification: Botanic—*Chrysanthemum indicum.*

*Flower*

Blooming habit: Blooms continuously from early September until a killing frost. Observations were made in the vicinity of Barberton, Ohio, in September.

Bud:
- *Size.*—Large.
- *Form.*—Globular.
- Wet weather causes rot and hot weather delays flowering.

Color:
- *When sepals first divide.*—5Y 9/9 Brilliant Yellow.
- *When petals begin to unfurl.*—7.5Y 9/8 Brilliant Greenish Yellow.
- *When half blown.*—Inside of petals—7/5Y 9/8 Brilliant Greenish Yellow. Reverse of petals—between 7/5Y 9/8 Brilliant Greenish Yellow and 5Y 9/9 Brilliant Yellow.
- *Sepals.*—Smooth edge.
- *Calyx.*—Shape—apple. Size—broad. Aspect—hairy.
- *Peduncle.* — Length — medium. Aspect — smooth. Strength—stiff, erect. Bud opens well but hot weather tends to delay flowering.

Bloom:
- *Size.*—Large. Average size when fully expanded—5½".
- *Borne.*—Clusters and rounded.
- *Stems.*—Long and strong.
- *Form.*—When first open—globular. Permanence—retains its form to the end.
- *Petalage.*—Very double with too many petals to count under normal conditions.
- *Color.*—Center of flower—5Y 9/9 Brilliant Yellow. Outer petals—7.5Y 9/8 Brilliant Greenish Yellow. Base of petals—between 5Y 8/12 and 5Y 9/9 Brilliant Yellow. Inside of petals—7.5Y 9/8 Brilliant Greenish Yellow. Reverse of petals—between 7/5Y 9/8 and 5Y 9/9 Brilliant Yellow. General tonality from a distance—between 5Y 9/9 Brilliant Yellow and 5Y 8/12 Vivid Yellow.
- *Discoloration.*—General tonality at end of: First week—5Y 8/12 Vivid Yellow. Second week—5Y 9/9 Brilliant Yellow. Third week—between 5Y 9/9 Brilliant Yellow and 7.5Y 9/8 Brilliant Greenish Yellow.

Petals:
- *Texture.*—Thick and leathery. Wet weather tends to rot, hot weather tends to burn.
- *Appearance.*—Inside—satiny. Outside—shiny.
- *Form.*—Oval.
- *Arrangement.*—Irregular.
- *Persistence.*—Hang on and dry.
- *Fragrance.*—None.
- *Lastingness.*—On the plant—long. As cut flowers—long.

Genital organs:

*Stamens, anthers.*—Small and many.

*Arrangement.*—Mixed with petaloids.

*Stamens, filaments.*—Medium.

*Styles.*—Bunched and of medium length.

Plant:

*Form.*—Shrub.

*Growth.*—Vigorous.

*Height.*—30 inches.

Foliage: Leaflets are in singlets.

*Size.*—Large.

*Quantity.*—Normal.

*Shape.*—Oval indented.

*Texture.*—Glossy.

*Ribs and veins.*—Ordinary.

*Stipules.*—Short and smooth.

I claim:

A new and distinct variety of chrysanthemum plant substantially as herein disclosed, characterized as to novelty by the brilliant to vivid yellow color of its blooms, the very double petalage, its strong habit of growth with blooms on long strong stems, and very early, continuous and long blooming period.

No references cited.